US00PP08005P

United States Patent [19]

Hofmann

[11] Patent Number: Plant 8,005

[45] Date of Patent: Oct. 13, 1992

[54] VARIETY OF GERANIUM NAMED PRECIOUS

[75] Inventor: Christa Hofmann, Dresden, Fed. Rep. of Germany

[73] Assignee: Oglevee Ltd., Connellsville, Pa.

[21] Appl. No.: 633,286

[22] Filed: Dec. 24, 1990

[51] Int. Cl.[5] ..... A01H 5/00

[52] U.S. Cl. ..... Plt./87.12

[58] Field of Search ..... Plt./68

[56] References Cited

U.S. PATENT DOCUMENTS

P.P. 7,343 10/1990 Craig et al. ..... Plt. 68

*Primary Examiner*—James R. Feyrer

*Attorney, Agent, or Firm*—Webb, Burden, Ziesenheim & Webb

[57] ABSTRACT

This new cultivar is characterized by its unique color, a light orchid with a touch of white in the center of each floret contrasted against the deep green foliage. It is also characterized by a more than usual number of smaller individual flower heads. The variety maintains its compact, uniform shape. Further, indoors the variety blooms early with many, medium sized blossoms making it a good cutting producer.

1 Drawing Sheet

BACKGROUND OF THE INVENTION

The present invention comprises a new and distinct cultivar of *Pelargonium*×*hortorum* known by the varietal name Precious (Oglevee No. 7023, V.E.B. Code P-25) formerly Krystal. The new variety was discovered in a selected breeding program in 1985 in Dresden, East Germany. The new variety is a selection from the crossing of PAC Rosalie, PAC Yvonne, inbreed lines and rose colored breeding stocks. The new variety was first asexually reproduced by cuttings at VEB Saat-und Pflanzgut, Ex-und Import, Moosdorfstrasse 3, 1193 Berlin, East Germany. The new variety has been asexually reproduced by cuttings at Oglevee Ltd. in Connellsville, Penn. over a several year period. It has also been trial and field tested at Connellsville and has been found to retain its distinctive characteristics through successive propagations.

The cultivar when grown in a glass greenhouse in Connellsville, Penn. using natural light and 60° F. night, 68° F. day and 71° F. vent, has a response time of six weeks from a rooted cutting to flowering in a 10 cm. pot. The response time was determined on plants grown in soilless media employing constant fertilizer 200 parts per million of nitrogen and potassium in full light. The rooted cuttings were potted Feb. 14, 1990 and flowered on Apr. 1, 1990.

DESCRIPTION OF THE DRAWING

FIG. 1 of the accompanying photographic drawing illustrates the new cultivar the color being as nearly true as possible with color illustrations of this type.

DESCRIPTION OF THE NEW PLANT

The following detailed description sets forth the characteristics of the new cultivar. The data which defines these characteristics were collected by asexual reproductions carried out by Oglevee Ltd. in Connellsville, Penn. The plant history was taken on six weeks plants blossomed under natural light in a greenhouse and the color readings were taken indoors under 100-125 foot candles of florescent cool white light. Color references are primarily to the R.H.S. Colour Chart of The Royal Horticultural Society of London.

THE PLANT

Classification:

*Botanical.*—*Pelargonium*×*hortorum.*

*Commercial.*—Zonal Geranium.

Form: Compact mound habit, basal branching.

*Height.*—19.0 to 20.0 cm. from media surface.

*Growth.*—Free and early flowering, basal branching, strong but compact habit.

Strength: Keeps its compact mound shape throughout the growing season.

Foliage: Little or no zoning; stalked leaf attachment.

Leaves:

*Size.*—6.5 to 10.0 cm. across.

*Shape.*—Reniform; cordate base.

*Margin.*—Crenate.

*Texture.*—Slightly pubescent, leathery appearance.

*Color.*—Top: Green group 137C. Bottom: Yellow/green group 146B.

*Ribs and veins.*—Palmate venation Color: Yellow/-green group 146C.

Petioles: Color: Yellow/green group 146B. Length: 5.0 to 10.0 cm. in length.

Stem:

*Color.*—Yellow/green group 146B.

*Internodes.*—2.5 to 5.0 cm. in length.

THE BUD

Shape: Hemispherical cluster; upright.

Size: 2.0 to 4.0 cm. across.

INFLORESCENCE

Blooming habit: Continuous blooming; many hemispherical clusters; semi-double; self-cleaning.

Size: 9.5 to 10.5 cm. across at the widest point.

Borne: Umbel; florets on pedicel, pedicel on peduncle; 6.5 to 11.0 cm. above foliage canopy.

*Form.*—Flat to slightly cupped.

*Color.*—Top: Purple group 75B along with a blotch of white on upper two petals giving the appearance of a white eye. Bottom: Purple group 75C.

*Petals.*—Obovate; separate, not united; margin entire, 6 to 8 in number.

*Size.*—4.0 to 5.0 cm. across.

*Texture and appearance.*—Smooth and satiny. Appearance from a distance, delicate orchid bloom accented by a small white eye flowering above a canopy of deep forest green foliage.

Petaloids:

*Quantity.*—1 to 3 in number.

*Shape.*—Elongated; twisted; some resemble petals except for deformed shape and pollen attached.

*Color.*—Purple group 75B.

Pedicel:

*Length.*—2.0 to 2.8 cm.

*Color.*—Bi-color; Greyed/purple group 183A reprsents most of the pedicel except the end that attaches to the peduncle which is Yellow/green group 146C.

Peduncle:

*Color.*—Yellow/green group 146B.

*Length.*—13.5 to 18.5 cm.

Disease resistance: Not known.

Lasting quality: This variety has been trialed outdoors in the summers of 1988 and 1989 and has stood up well under the stress of heat, wind and rain.

REPRODUCTIVE ORGANS

Stamens:

*Anthers.*—2.0 to 3.0 mm. in length.

*Filaments.*—6.0 to 8.0 mm in length; usually white except at the anther end which is pink.

*Pollen.*—Golden brown (Greyed/orange group 175C).

Pistils:

*Number.*—One

*Length.*—8.0 to 10.0 mm.

*Stigma.*—One; 5-6 parted; red-purple in color.

*Style.*—3.0 to 5.0 mm. in length; red-purple in color.

Ovaries: 4.0 to 5.0 mm. in length; 2.0 to 3.0 mm. in width; superior, pale green and very pubescent.

Fruit: None observed.

GENERAL CHARACTERISTICS

This variety displays a unique and new color. The light orchid color with a touch of white in the center of each floret is a dramatic contrast to the deep green foliage.

Outdoor performance has been excellent. Although exposed to extreme conditions, (high temperatures, excessive amounts of rain, etc.) this variety continues to bloom. The individual flower heads may be smaller but there are many more of them than is seen on the typical zonal. The plant habit maintains its compact uniform shape throughout the outdoor season.

Indoor performance is also exceptional. It is early blooming, again with many, medium sized blossoms. The good basal branching fills out the 4" pot and permits this variety to be a good cutting producer.

I claim:

1. A new and distinct variety of Geranium plant, substantially as shown and described.

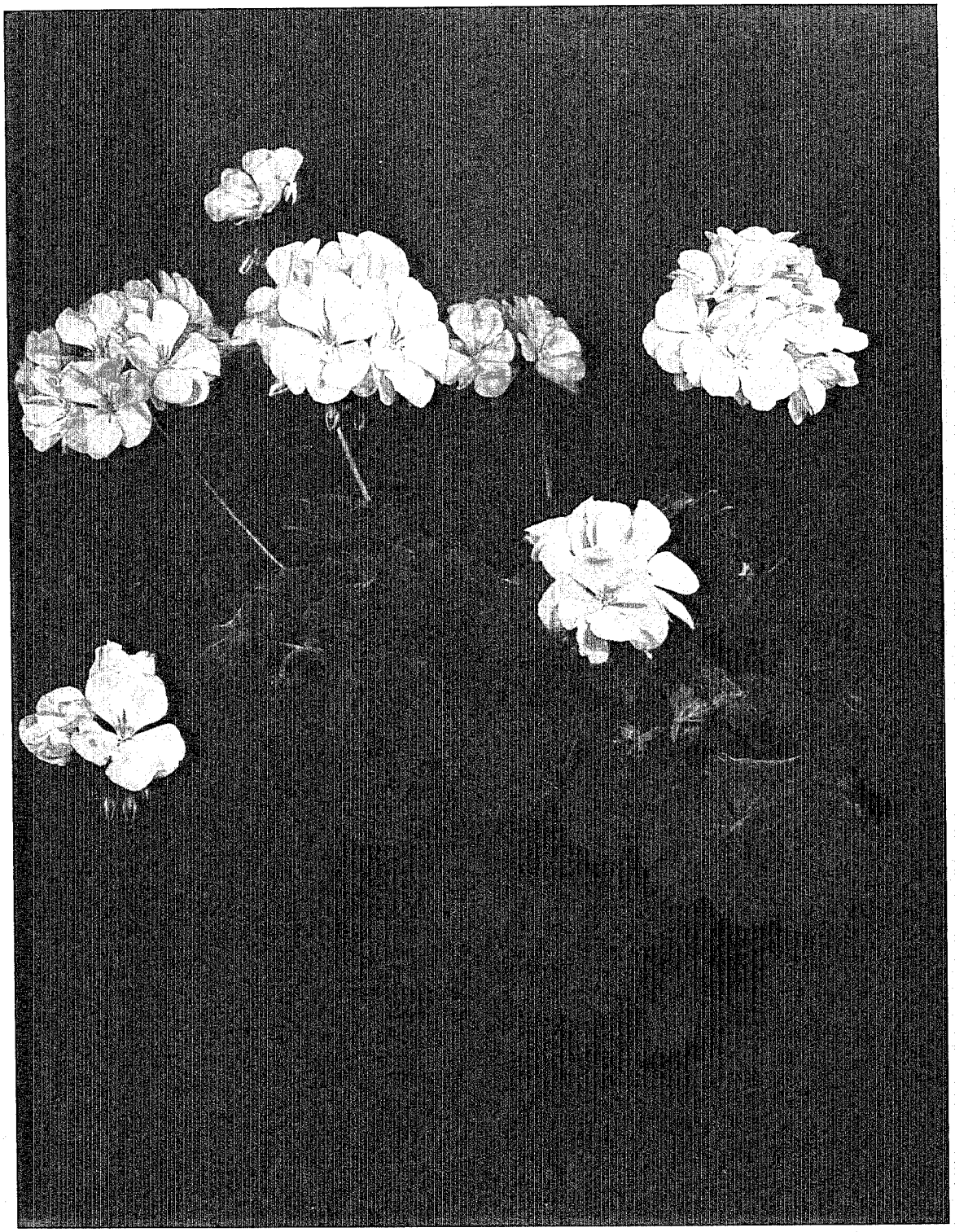

* * * * *